(12) United States Patent
Murakami et al.

(10) Patent No.: US 8,791,295 B2
(45) Date of Patent: Jul. 29, 2014

(54) METHOD OF PRODUCING PURIFIED OPTICALLY ACITVE 4-AMINO-3-(SUBSTITUTED PHENYL)BUTANOIC ACID COMPOUND

(75) Inventors: Kazuo Murakami, Kashiba (JP); Masahiro Takeda, Nishinomiya (JP); Hirofumi Kato, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 667 days.

(21) Appl. No.: 12/997,121

(22) PCT Filed: Sep. 22, 2008

(86) PCT No.: PCT/JP2008/067595
§ 371 (c)(1),
(2), (4) Date: Dec. 9, 2010

(87) PCT Pub. No.: WO2009/153889
PCT Pub. Date: Dec. 23, 2009

(65) Prior Publication Data
US 2011/0087049 A1    Apr. 14, 2011

(30) Foreign Application Priority Data
Jun. 19, 2008  (JP) .................. 2008-160314

(51) Int. Cl.
*C07C 227/40* (2006.01)
(52) U.S. Cl.
USPC .......................................... 562/443
(58) Field of Classification Search
USPC ........................................... 562/443
See application file for complete search history.

(56) References Cited

U.S. PATENT DOCUMENTS

| | | | |
|---|---|---|---|
| 7,012,130 B1 | 3/2006 | Carcagno et al. | |
| 2009/0137819 A1* | 5/2009 | Yasuoka et al. | 548/531 |

FOREIGN PATENT DOCUMENTS

| | | |
|---|---|---|
| DE | 2 12 508 A1 | 8/1984 |
| JP | 45-016692 | 6/1970 |
| JP | 57-102851 A | 6/1982 |
| JP | 60-32752 | 2/1985 |
| JP | 61-501704 | 8/1986 |
| JP | 63/57560 | 3/1988 |
| JP | 4-266864 | 9/1992 |
| JP | 6-306029 | 11/1994 |
| JP | 2007-332129 | 12/2007 |
| WO | WO 2007066828 A1 * | 6/2007 |

OTHER PUBLICATIONS

Office Action Japanese Patent Application No. JP 2008-160314 dated Jan. 22, 2013.
International Preliminary Report on Patentability (IPRP) in PCT/JP2008/067595 dated Feb. 8, 2011.
International Search Report in PCT/JP2008/067595 dated Nov. 25, 2008.
Okino, et al. "Enantio-and Diastereoselective Michael Reaction of 1,3-Dicarbonyl Compounds to Nitroolefins Catalyzed by a Bifunctional Thiourea" J. Am. Chem. Soc., 2005, vol. 127, pp. 119-125.

* cited by examiner

*Primary Examiner* — Porfirio Nazario Gonzalez
*Assistant Examiner* — Kofi Adzamli
(74) *Attorney, Agent, or Firm* — Foley & Lardner LLP

(57) ABSTRACT

A method of producing a purified optically active 4-amino-3-(substituted phenyl)butanoic acid compound which is characterized by comprising a step of making a crude optically active 4-amino-3-(substituted phenyl)butanoic acid compound contact an organic acid in the presence of water.

8 Claims, No Drawings

METHOD OF PRODUCING PURIFIED OPTICALLY ACITVE 4-AMINO-3-(SUBSTITUTED PHENYL)BUTANOIC ACID COMPOUND

TECHNICAL FIELD

The present invention relates to a method of producing a purified optically active 4-amino-3-(substituted phenyl)butanoic acid compound.

BACKGROUND ART (R)-4-amino-3-(4-chlorophenyl)butanoic acid which is a representative compound of optically active 4-amino-3-(substituted phenyl)butanoic acid compounds is useful as a reflux esophagitis remedy or antispasmodic.

With regard to a method of producing an optically active 4-amino-3-(substituted phenyl)butanoic acid compound, J. Am. Chem. Soc., 2005, 127, 119-125, JP No. Sho-45-16692B and WO2007/066828 disclose a method of reacting a 4-(substituted phenyl)pyrrolidin-2-one compound with a mineral acid such as hydrochloric acid.

With regard to a method of producing a purified optically active 4-amino-3-(substituted phenyl)butanoic acid compound from the resulting crude optically active 4-amino-3-(substituted phenyl)butanoic acid compound, JP No. Sho-45-16692B discloses a method of making an aqueous solution containing a hydrochloride of a crude optically active 4-amino-3-(substituted phenyl)butanoic acid compound contact an ion-exchange resin and concentrating the resulting solution, and recrystallizing the resulting crystal with water-alcohol.

DISCLOSURE OF THE INVENTION

The present invention provides:
(1) a method of producing a purified optically active 4-amino-3-(substituted phenyl)butanoic acid compound which is characterized by comprising a step of making a crude optically active 4-amino-3-(substituted phenyl)butanoic acid compound contact an organic acid in the presence of water;
(2) the method according to (1), wherein the organic acid is a carboxylic acid;
(3) the method according to (2), wherein the carboxylic acid is acetic acid;
(4) the method according to any of (1) to (3), wherein the amount of water used is 1 to 10 parts by weight, based on 1 part by weight of the crude optically active 4-amino-3-(substituted phenyl)butanoic acid compound;
(5) the method according to any of (1) to (4), wherein the amount of the organic acid used is 0.01 to 2 parts by weight, based on 1 part by weight of the crude optically active 4-amino-3-(substituted phenyl)butanoic acid compound;
(6) the method according to any of (1) to (5), wherein the optical purity of the crude optically active 4-amino-3-(substituted phenyl)butanoic acid compound is 90% e.e. or more;
(7) the method according to any of (1) to (6), which comprises a step of making the crude optically active 4-amino-3-(substituted phenyl)butanoic acid compound contact an aqueous solution of the organic acid; and
(8) the method according to any of (1) to (7), wherein the optically active 4-amino-3-(substituted phenyl)butanoic acid compound is (R)-4-amino-3-(4-chlorophenyl)butanoic acid or (S)-4-amino-3-(4-chlorophenyl)butanoic acid.

BEST MODES FOR CARRYING OUT THE INVENTION

The present invention is a method of producing a purified optically active 4-amino-3-(substituted phenyl)butanoic acid compound which is characterized by comprising a step of making a crude optically active 4-amino-3-(substituted phenyl)butanoic acid compound contact an organic acid in the presence of water.

The optically active 4-amino-3-(substituted phenyl)butanoic acid compound includes a compound represented by formula (1):

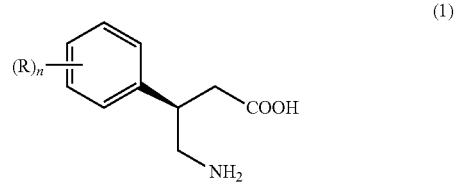

(wherein, R represents a halogen atom, an alkyl group having a carbon number of 1 to 20, an alkoxy group having a carbon number of 1 to 20, a haloalkyl group having a carbon number of 1 to 20 or a cycloalkyloxy group having a carbon number of 3 to 8, and n represents an integer of 1 to 3, when n is 2 or 3, Rs may be the same or different from each other, and two Rs may together form an alkylenedioxy group having a carbon number of 1 to 5), and a compound represented by formula (2):

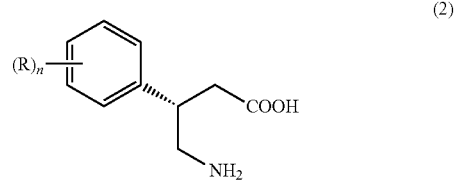

(wherein, R and n have the same meanings as described above).

The halogen atom includes a fluorine atom, a chlorine atom, a bromine atom and an iodine atom, preferably a chlorine atom and a bromine atom, and more preferably a chlorine atom.

The alkyl group having a carbon number of 1 to 20 includes linear or branched alkyl groups having a carbon number of 1 to 20 such as a methyl group, an ethyl group, a propyl group, an isopropyl group, a butyl group, a pentyl group, a hexyl group, a heptyl group, an octyl group, a decyl group, a nonyl group, an undecyl group and a dodecyl group, preferably alkyl groups having a carbon number of 1 to 6, and more preferably a methyl group and an ethyl group.

The alkoxy group having a carbon number of 1 to 20 includes linear or branched alkoxy groups having a carbon number of 1 to 20 such as a methoxy group, an ethoxy group, a propoxy group, an isopropoxy group, a butoxy group, a pentyloxy group, a hexyloxy group, a heptyloxy group, an octyloxy group, a decyloxy group, a nonyloxy group, an undecyloxy group and a dodecyloxy group, preferably alkoxy groups having a carbon number of 1 to 6, and more preferably a methoxy group.

The haloalkyl group having a carbon number of 1 to 20 includes groups obtained by substituting at least one hydrogen atom of the alkyl group having a carbon number of 1 to 20 with the halogen atom. Specific examples include a fluoromethyl group, a difluoromethyl group, a trifluoromethyl group, a 1-fluoromethyl group, a 2-fluoroethyl group, a 2,2-difluoroethyl group, a 2,2,2-trifluoroethyl group, a 1-fluoropropyl group, a 1-fluorobutyl group, a 1-fluoropentyl group, a 1-fluorohexyl group, a chloromethyl group, a dichloromethyl group, a trichloromethyl group, a 1-chloroethyl group, a 2-chloroethyl group, a 2,2-dichloroethyl group, a 2,2,2-trichloroethyl group, a 1-chloropropyl group, a 1-chlorobutyl group, a 1-chloropentyl group, a 1-chlorohexyl group, a bromomethyl group, a 1-bromoethyl group, a 2-bromoethyl group, a 1-bromopropyl group, an iodomethyl group, a 1-iodoethyl group, a 2-iodoethyl group, a 1-iodopropyl group, and the like, and preferably, a fluoromethyl group, a difluoromethyl group and a trifluoromethyl group.

The cycloalkyloxy group having a carbon number of 3 to 8 includes a cyclopropyloxy group, a cyclobutyloxy group, a cyclopentyloxy group, a cyclohexyloxy group, and the like, preferably cycloalkyloxy groups having 3 to 6, and more preferably, a cyclopentyloxy group.

The alkylenedioxy group having a carbon number of 1 to 5 to be formed by two Rs together includes linear or branched alkylenedioxy groups having a carbon number of 1 to 5 such as a methylenedioxy group, an ethylenedioxy group and a tetramethylenedioxy group, more preferably alkylenedioxy groups having a carbon number of 1 to 2, and preferably, a methylenedioxy group or an ethylenedioxy group.

The optically active 4-amino-3-(substituted phenyl)butanoic acid compound is preferably a compound represented by formula (1) or formula (2), wherein n is 1, and preferably a compound represented by formula (1) or formula (2), wherein n is 1, and R bonds to the 4-position.

The optically active 4-amino-3-(substituted phenyl)butanoic acid compound is preferably a compound represented by formula (1), wherein R is a halogen atom, and n is 1, and more preferably a compound represented by formula (1), wherein R is a halogen atom bonded to the 4-position, and n is 1.

The optically active 4-amino-3-(substituted phenyl)butanoic acid compound is preferably (R)-4-amino-3-(4-chlorophenyl)butanoic acid and (S)-4-amino-3-(4-chlorophenyl)butanoic acid, and particularly preferably (R)-4-amino-3-(4-chlorophenyl)butanoic acid.

The crude optically active 4-amino-3-(substituted phenyl)butanoic acid compound may be a mixture of two optical isomers, which contains one optical isomer more than the other optical isomer. The optical purity of the compound is preferably 90% e.e. or more.

The organic acid includes carboxylic acids such as formic acid, acetic acid, propionic acid, succinic acid, fumaric acid, lactic acid, malic acid, tartaric acid, and citric acid, and preferably acetic acid in that it is easily available and inexpensive.

The amount of the organic acid used is usually 0.01 to 2 parts by weight, preferably 0.01 to 1 part by weight, more preferably 0.02 to 0.5 parts by weight, and particularly preferably 0.02 to 0.3 parts by weight, based on 1 part by weight of the crude optically active 4-amino-3-(substituted phenyl)butanoic acid compound.

The amount of water used is usually 1 to 10 parts by weight, preferably 3 to 8 parts by weight, and more preferably 4 to 6 parts by weight, based on 1 part by weight of the crude optically active 4-amino-3-(substituted phenyl)butanoic acid compound.

The order of the contact of the crude optically active 4-amino-3-(substituted phenyl)butanoic acid compound with the organic acid and water is not limited. In addition, the organic acid may be preliminarily mixed with water to prepare an aqueous solution of the organic acid, and the aqueous solution of the organic acid may be made to contact the crude optically active 4-amino-3-(substituted phenyl)butanoic acid compound.

The contact temperature is usually from 0 to 100° C., preferably from 10 to 90° C., and more preferably from 20 to 80° C. The contact time is usually from 10 minutes to 24 hours.

After the contact, a purified optically active 4-amino-3-(substituted phenyl)butanoic acid compound is obtained, for example, by filtrating the resulting mixture. The filtration temperature is usually from 0 to 100° C., and preferably from 0 to 30° C.

The purified optically active 4-amino-3-(substituted phenyl)butanoic acid compound with a higher optical purity than the used crude optically active 4-amino-3-(substituted phenyl)butanoic acid compound is thus obtained.

The crude optically active 4-amino-3-(substituted phenyl)butanoic acid compound can be produced by a known method described in J. Am. Chem. Soc., 2005, 127, 119-125, Japanese Examined Patent Publication No. 45-16692, WO2007/066828, or the like.

EXAMPLES

The present invention will be described in more detail by the following examples, but the present invention is not limited to the examples. The yield and optical purity of (R)-4-amino-3-(4-chlorophenyl)butanoic acid were each calculated by high-performance liquid chromatography (Conditions 1 as follows) and high-performance liquid chromatography (Conditions 2 as follows).

<Conditions 1>
  Column: CHIRALPAK C8 DD (4.6 mm×150 mm, φ5 μm)
  Mobile Phase: Solution A: 0.1% phosphoric acid aqueous solution, Solution B: acetonitrile
  Mobile Phase Gradient: 0 min (10% Solution B)→20 min (60% Solution B)→35 min (60% Solution B)→35.1 min (10% Solution B)→45 min
  Column Temperature: 35° C.
  Flow Rate: 1 ml/min
  Detector: UV 210 nm
<Conditions 2>
  Column: CROWNPAK CR (+) (4.6 mm×250 mm)
  Mobile Phase: HClO$_4$ aqueous solution (pH2)
  Flow Rate: 2.0 ml/min
  Column Temperature: 40° C.
  Detector: UV 220 nm Reference Example 1

(1) 200.14 g (1.36 mol) of 4-chlorobenzaldehyde, 153.4 g (1.43 mol) of benzylamine, and 1066.8 g of acetic acid were mixed. To the resulting solution was dropped 325.7 g (5.34 mol) of nitromethane at 78 to 80° C. over a period of 2 hours and 50 minutes. The resulting mixture was stirred at about 79° C. for 40 minutes, and thereafter, 1016 g of water was dropped at about 50° C. over a period of 2 hours and 25 minutes. The resulting mixture was cooled to about 10° C. over a period of 1 hour and 50 minutes and stirred at 6 to 10° C. for 1 hour and 50 minutes. The deposited crystals were filtrated, and the resulting crystals were washed with 1016.2 g of water. The resulting crystals were mixed with 572.8 g of toluene adjusted to about 50° C., to obtain a solution. The resulting solution was allowed to stand still, and thereafter, the aqueous layer was separated. The resulting toluene layer was washed with 330.8 g of water, to obtain 803.24 g of the toluene layer containing 253.8 g of 4-chloro-trans-β-nitrostyrene. Yield: 97.1%.

(2) Under a nitrogen atmosphere, a solution obtained by dissolving 34 g (0.0082 mol) of (R,R)-trans-1-[3,5-bis(trifluoromethyl)phenyl]-3-[2-(N,N-dimethylamino)cyclohexyl]thiourea into 100 g of toluene and 3730 g of a toluene solution containing 1492 g (8.1 mol) of 4-chloro-trans-β-nitrostyrene obtained by carrying out the same as in (1) described above were mixed. To the resulting mixture was added 3905 g (24.4 mol) of diethyl malonate at about 20° C. The resulting mixture was stirred for 24 hours. The resulting reaction mixture was concentrated under reduced pressure, to obtain 5648 g of a toluene solution containing 2598 g of ethyl (S)-2-ethoxycarbonyl-4-nitro-3-phenylbutyrate. Yield: 93%.

(3) Under a nitrogen atmosphere, 5646 g of a toluene solution containing the ethyl (S)-2-ethoxycarbonyl-4-nitro-3-phenylbutyrate obtained in (2) described above and 519 g of a Raney nickel catalyst (manufactured by Kawaken Fine Chemicals Co., Ltd.) were added to 7144 g of 2-propanol, and the mixture was reacted at about 70° C. under a hydrogen pressure of 0.5 MPa (gauge pressure). After completion of the reaction, the reaction mixture was filtrated to remove the catalyst, and the resulting filtrate was concentrated under reduced pressure. To the resulting residue was added 3392 g of 1,2-dichlorobenzene, to obtain 7035 g of a solution containing 1618 g of ethyl (3S,4R)-4-(4-chlorophenyl)-2-oxopyrrolidine-3-carboxylate.

(4) To 7035 g of a solution containing the ethyl (3S,4R)-4-(4-chlorophenyl)-2-oxopyrrolidine-3-carboxylate obtained in (3) described above were added 2425 g of water and 3236 g of 35% hydrochloric acid. The resulting mixture was stirred at about 100° C. for 24 hours. The resulting reaction mixture was cooled and then separated into an organic layer and an aqueous layer. The resulting aqueous layer was washed with 3392 g of 1,2-dichlorobenzene. The resulting aqueous layer was refluxed. After confirming that (R)-4-(4-chlorophenyl)pyrrolidin-2-one in the aqueous layer was 0.5% or less, 8417 g of toluene was added thereto at 70 to 90° C. The resulting mixture was concentrated until the inside temperature reached to 111° C. To the resulting concentrated residue were added 143 g of water and 2494 g of acetonitrile, and the mixture was cooled. The resulting mixture was stirred at about 20° C. for 1 hour. The mixture was filtrated, and the resulting solid was washed with a mixed solution of 63 g of water and 2494 g of acetonitrile and further dried, to obtain 1361 g of (R)-4-amino-3-(4-chlorophenyl)butanoic acid hydrochloride.

(5) 1361 g of the (R)-4-amino-3-(4-chlorophenyl)butanoic acid hydrochloride obtained in (4) described above and 4083 g of water were mixed. To the resulting solution was added 14 g of activated carbon, thereafter, the mixture was filtrated, and the activated carbon was washed with 1361 g of water. The solution obtained by dissolving 224 g of sodium hydroxide into 2722 g of water was dropped into the resulting filtrate at about 70° C. to adjust pH to 5 to 6. The resulting mixture was cooled to about 20° C. and filtrated. The resulting solid was washed with 2042 g of water and further dried under reduce pressure, to obtain 1163 g of crude (R)-4-amino-3-(4-chlorophenyl)butanoic acid. Optical Purity: 97.8%.

Example 1

Mixed were 10.06 g of the crude (R)-4-amino-3-(4-chlorophenyl)butanoic acid obtained in Reference Example 1, 50 g of water and 1 g of acetic acid. The resulting mixture was stirred at about 70° C. for 60 minutes and then stirred at about 25° C. for 30 minutes. The resulting mixture was filtrated, and the resulting solid was dried, to obtain purified (R)-4-amino-3-(4-chlorophenyl)butanoic acid.
Yield: 92%. Optical Purity: 99.2%.

Example 2

Mixed were 10.06 g of the crude (R)-4-amino-3-(4-chlorophenyl)butanoic acid obtained in Reference Example 1, 50 g of water and 0.66 g of acetic acid. The resulting mixture was stirred at about 70° C. for 60 minutes and then stirred at about 25° C. for 30 minutes. The resulting mixture was filtrated, and the resulting solid was dried, to obtain purified (R)-4-amino-3-(4-chlorophenyl)butanoic acid.
Yield: 92.1%. Optical Purity: 99.3%.

Example 3

Mixed were 10.06 g of the crude (R)-4-amino-3-(4-chlorophenyl)butanoic acid obtained in Reference Example 1, 50 g of water and 0.33 g of acetic acid. The resulting mixture was stirred at about 70° C. for 60 minutes and then stirred at about 25° C. for 30 minutes. The resulting mixture was filtrated, and the resulting solid was dried, to obtain purified (R)-4-amino-3-(4-chlorophenyl)butanoic acid.
Yield: 94.2%. Optical Purity: 99.2%.

Comparative Example 1

Mixed were 10.0 g of the crude (R)-4-amino-3-(4-chlorophenyl)butanoic acid obtained in Reference Example 1 and 50 g of water, and to the resulting mixture was added hydrochloric acid to adjust pH to 5.0. The resulting mixture was stirred at about 70° C. for 60 minutes and then stirred at about 25° C. for 30 minutes. The resulting mixture was filtrated, and the resulting solid was dried, to obtain (R)-4-amino-3-(4-chlorophenyl)butanoic acid.
Yield: 95.4%. Optical Purity: 97.1%.

Comparative Example 2

Mixed were 10.0 g of the crude (R)-4-amino-3-(4-chlorophenyl)butanoic acid obtained in Reference Example 1 and 50 g of water, and to the resulting mixture was added sodium hydroxide to adjust pH to 8.0. The resulting mixture was stirred at about 70° C. for 60 minutes and then stirred at about 25° C. for 30 minutes. The resulting mixture was filtrated, and the resulting solid was dried, to obtain (R)-4-amino-3-(4-chlorophenyl)butanoic acid.
Yield: 97.6%. Optical Purity: 98.5%.

Comparative Example 3

Mixed were 10.0 g of the crude (R)-4-amino-3-(4-chlorophenyl)butanoic acid obtained in Reference Example 1 and 50 g of water, and to the resulting mixture was added sodium hydroxide to adjust pH to 9.0. The resulting mixture was stirred at about 70° C. for 60 minutes and then stirred at about 25° C. for 30 minutes. The resulting mixture was filtrated, and the resulting solid was dried, to obtain (R)-4-amino-3-(4-chlorophenyl)butanoic acid.
Yield: 95.3%. Optical Purity: 97.9%.

Comparative Example 4

Mixed were 10.0 g of the crude (R)-4-amino-3-(4-chlorophenyl)butanoic acid obtained in Reference Example 1 and 50 g of water. The resulting mixture was stirred at about 70° C. for 60 minutes and then stirred at about 25° C. for 30 minutes. The resulting mixture was filtrated, and the resulting solid was dried, to obtain (R)-4-amino-3-(4-chlorophenyl)butanoic acid.

Yield: 94.5%. Optical Purity: 97.5%.

Industrial Applicability

According to the present invention, an optically active 4-amino-3-(substituted phenyl)butanoic acid compound with a higher optical purity can be easily obtained.

The invention claimed is:

1. A method of producing a purified optically active 4-amino-3-(substituted phenyl)butanoic acid compound comparing a step of mixing a crude optically active 4-amino-3-(substituted phenyl)butanoic acid compound with an organic acid in water and a step of filtrating the resulting mixture.

2. The method according to claim 1, wherein the organic acid is a carboxylic acid.

3. The method according to claim 2, wherein the carboxylic acid is acetic acid.

4. The method according to claim 1, wherein the amount of water used is 1 to 10 parts by weight, based on the weight of the crude optically active 4-amino-3-(substituted phenyl)butanoic acid compound.

5. The method according to claim 1, wherein the amount of the organic acid used is 0.01 to 2 parts by weight, based on the weight of the crude optically active 4-amino-3-(substituted phenyl)butanoic acid compound.

6. The method according to claim 1, wherein the optical purity of the crude optically active 4-amino-3-(substituted phenyl)butanoic acid compound is 90% e.e. or more.

7. The method according to claim 1, which comprises a step of mixing the crude optically active 4-amino-3-(substituted phenyl)butanoic acid compound with an aqueous solution of the organic acid.

8. The method according to claim 1, wherein the optically active 4-amino-3-(substituted phenyl)butanoic acid compound is (R)-4-amino-3-(4-chlorophenyl)butanoic acid or (S)-4-amino-3-(4-chlorophenyl)butanoic acid.

* * * * *